US008672934B2

(12) United States Patent
Benamou et al.

(10) Patent No.: US 8,672,934 B2
(45) Date of Patent: Mar. 18, 2014

(54) METHOD FOR ADJUSTING SOURCE IMPEDANCE AND MAXIMIZING OUTPUT BY RF GENERATOR

(75) Inventors: Steffan A. Benamou, San Jose, CA (US); Andrew J. Hamel, San Mateo, CA (US); David Hoffman, Santa Cruz, CA (US); David I. Brubaker, San Carlos, CA (US)

(73) Assignee: Stryker Corporation, Kalamazoo, MI (US)

( * ) Notice: Subject to any disclaimer, the term of this patent is extended or adjusted under 35 U.S.C. 154(b) by 959 days.

(21) Appl. No.: 12/661,340

(22) Filed: Mar. 16, 2010

(65) Prior Publication Data
US 2010/0241116 A1    Sep. 23, 2010

Related U.S. Application Data

(60) Provisional application No. 61/210,330, filed on Mar. 17, 2009.

(51) Int. Cl.
*A61B 18/18* (2006.01)
(52) U.S. Cl.
USPC ............................................. 606/34; 606/42
(58) Field of Classification Search
USPC .............................. 606/34, 27, 42
See application file for complete search history.

(56) References Cited

U.S. PATENT DOCUMENTS

| 3,923,063 | A | | 12/1975 | Andrews et al. |
| 4,574,801 | A | | 3/1986 | Manes |
| 4,658,819 | A | | 4/1987 | Harris et al. |
| 4,739,759 | A | | 4/1988 | Rexroth et al. |
| 5,300,068 | A | * | 4/1994 | Rosar et al. ..................... 606/34 |
| 5,383,874 | A | * | 1/1995 | Jackson et al. ..................... 606/1 |
| 5,514,129 | A | | 5/1996 | Smith |
| 5,871,469 | A | | 2/1999 | Eggers et al. |
| 5,888,198 | A | | 3/1999 | Eggers et al. |
| 5,951,545 | A | * | 9/1999 | Schilling et al. ................ 606/37 |
| 5,957,969 | A | * | 9/1999 | Warner et al. ................. 607/156 |
| 5,983,141 | A | | 11/1999 | Sluijter et al. |
| 6,017,354 | A | * | 1/2000 | Culp et al. ..................... 606/170 |
| 6,019,757 | A | * | 2/2000 | Scheldrup ....................... 606/49 |
| 6,074,386 | A | * | 6/2000 | Goble et al. ..................... 606/34 |
| 6,161,048 | A | | 12/2000 | Sluijter et al. |

(Continued)

OTHER PUBLICATIONS

"SERFAS Energy System" Stryker Endoscopy, publicly disclosed before Mar. 2008.

*Primary Examiner* — Linda Dvorak
*Assistant Examiner* — Jocelyn D Ram
(74) *Attorney, Agent, or Firm* — Flynn, Thiel, Boutell & Tanis, P.C.

(57) ABSTRACT

An electrosurgical system includes an electrosurgical probe connected to a control console, wherein the probe is capable of coagulating and ablating tissue depending on a selected operating mode. Before operating the system, probe-specific data stored in a memory device associated with the probe is read by a processing device in the console. The data includes source impedance values specific to a coagulation or cutting mode of operation. A constant duty cycle value for a modulated cutting mode also is provided. Depending on the operating mode selected, an RF generator adjusted to have a predetermined source impedance value provides a voltage value to the probe. During the duty-cycled mode, the RF generator generates an instantaneous voltage value output for a duty cycle portion that is less than 100% of a time period, which value is no less than a maximum continuous average voltage value for the electrosurgical probe.

20 Claims, 8 Drawing Sheets

(56) References Cited

U.S. PATENT DOCUMENTS

| | | | |
|---|---|---|---|
| 6,190,379 B1 * | 2/2001 | Heuser et al. | 606/28 |
| 6,238,388 B1 * | 5/2001 | Ellman et al. | 606/37 |
| 6,246,912 B1 | 6/2001 | Sluijter et al. | |
| 6,259,952 B1 | 7/2001 | Sluijter et al. | |
| 6,436,097 B1 | 8/2002 | Nardella | |
| 6,582,427 B1 * | 6/2003 | Goble et al. | 606/37 |
| 6,652,514 B2 | 11/2003 | Ellman et al. | |
| 6,666,860 B1 * | 12/2003 | Takahashi | 606/34 |
| 6,712,813 B2 | 3/2004 | Ellman et al. | |
| 6,994,707 B2 | 2/2006 | Ellman et al. | |
| 7,154,378 B1 | 12/2006 | Ertas et al. | |
| 7,195,627 B2 | 3/2007 | Amoah et al. | |
| 7,211,081 B2 | 5/2007 | Goble | |
| 7,214,224 B2 * | 5/2007 | Goble | 606/34 |
| 7,244,257 B2 | 7/2007 | Podhajsky et al. | |
| 2002/0029036 A1 * | 3/2002 | Goble et al. | 606/38 |
| 2004/0220602 A1 | 11/2004 | Deng et al. | |
| 2005/0004564 A1 | 1/2005 | Wham et al. | |
| 2006/0025759 A1 * | 2/2006 | Ellman et al. | 606/37 |
| 2006/0235377 A1 | 10/2006 | Earley et al. | |
| 2007/0093800 A1 | 4/2007 | Wham et al. | |
| 2007/0129716 A1 | 6/2007 | Daw et al. | |
| 2007/0129726 A1 | 6/2007 | Eder et al. | |
| 2007/0167941 A1 | 7/2007 | Hamel et al. | |
| 2007/0167942 A1 | 7/2007 | Rick | |
| 2007/0173803 A1 * | 7/2007 | Wham et al. | 606/34 |
| 2007/0173805 A1 * | 7/2007 | Weinberg et al. | 606/34 |
| 2007/0173809 A1 * | 7/2007 | Goble | 606/37 |
| 2008/0039831 A1 | 2/2008 | Odom et al. | |
| 2009/0076492 A1 * | 3/2009 | Behnke | 606/33 |
| 2010/0324548 A1 * | 12/2010 | Godara et al. | 606/34 |
| 2013/0023867 A1 * | 1/2013 | Collins | 606/33 |
| 2013/0096556 A1 * | 4/2013 | Lorang et al. | 606/42 |

\* cited by examiner

METHOD FOR ADJUSTING SOURCE IMPEDANCE AND MAXIMIZING OUTPUT BY RF GENERATOR

CROSS REFERENCE TO RELATED APPLICATION

This application claims the benefit of U.S. Provisional Application Ser. No. 61/210,330, filed Mar. 17, 2009, which is incorporated herein by reference in its entirety.

FIELD OF THE INVENTION

This invention is related generally to an electrosurgical system having an RF generator with a variable source impedance for providing a maximum RF power value to an RF probe, and having a cutting duty cycle value that provides increased instantaneous voltage to the probe for cutting tissue.

BACKGROUND OF THE INVENTION

Endoscopy in the medical field allows internal features of the body of a patient to be viewed without the use of traditional, fully-invasive surgery. Endoscopic imaging systems enable a user to view a surgical site and endoscopic cutting tools enable non-invasive surgery at the site. For instance, an RF generator provides energy to a distal end tip of an RF probe within the surgical site. In one mode, the RF probe provides RF energy at a power level to ablate or otherwise surgically remove tissue. In another instance, RF energy is provided to the RF probe in order to coagulate the tissue at the surgical site to minimize bleeding thereat.

Tissue ablation is achieved when a high power electrical signal having a sufficiently large voltage is generated by the control console and directed to the attached probe. Application of the high power signal to the probe results in a large voltage difference between the two electrodes located at the tip of the probe (presuming a bipolar probe), with the active electrode being generally 200 volts more than the passive or return electrode. This large voltage difference leads to the formation of an ionized region between the two electrodes, establishing a high energy field at the tip of the probe. Applying the tip of the probe to organic tissue leads to a rapid rise in the internal temperature of the cells making up the neighboring tissue. This rapid rise in temperature nearly instantaneously causes the intracellular water to boil and the cells to burst and vaporize, a process otherwise known as tissue ablation. An electrosurgical "cut" is thus made by the path of disrupted cells that are ablated by the extremely hot, high energy ionized region maintained at the tip of the probe. An added benefit of electrosurgical cuts is that they cause relatively little bleeding, which is the result of dissipation of heat to the tissue at the margins of the cut that produces a zone of coagulation along the cut edge.

In contrast to tissue ablation, the application of a low power electrical signal having a relatively low voltage to the active electrode located at the tip of the probe results in coagulation. Specifically, the lower voltage difference established between the active and return electrodes results in a relatively slow heating of the cells, which in turn causes desiccation or dehydration of the tissue without causing the cells to burst.

Basic operation of an electrosurgical system can be analyzed in view of at least two relationships.

The first relationship is described by Ohm's law, which in simplest terms, is represented by the equation $V=I \times R$ or alternatively $V=(I \times Z)$, where:

I=electrical current;
R=resistance or impedance to the current (hereafter referred to as Impedance (Z), which includes capacitive and inductive loading); and
V=voltage or force that "pushes" the current through the impedance.

The second relationship is the definition of power (P), which can be calculated by the equation ($P=I \times V$). The resultant product of current I and voltage V represents the amount of energy that is transferred within a defined period of time.

FIGS. 1 and 2 correspond to FIGS. 1 and 2 of U.S. Patent Publication 2007/0167941, the disclosure of which is hereby incorporated by reference.

As illustrated in FIG. 1, a typical electrosurgical system 10 includes an electrosurgical probe 12 (hereafter referred to simply as "probe") and a control console or controller 14. The probe 12 generally comprises an elongated shaft 16 with a handle 18 at one end and a tip 20 at the opposite end. A single active electrode 19 is provided at the tip 20 if the probe 12 is of a "monopolar" design. Conversely, the probe 12 may be provided with both an active electrode 19 and a return electrode 21 at the tip 20 if the probe is "bipolar" in design. The probe 12 connects to control console 14 by means of a detachable cable 22. The current for energizing the probe 12 comes from control console 14. When actuated, the control console 14 generates a power signal suitable for applying across the electrode(s) located at the tip 20 of the probe 12. Specifically, current generated by the control console 14 travels through the cable 22 and down the shaft 16 to tip 20, where the current subsequently energizes the active electrode 19. If the probe 12 is monopolar, the current will depart from tip 20 and travel through the patient's body to a remote return electrode, such as a grounding pad. If the probe 12 is bipolar, the current will primarily pass from the active electrode 19 located at tip 20 to the return electrode 21, also located at tip 20, and subsequently along a return path back up the shaft 16 and through the detachable cable 22 to the control console 14.

Configuration of the control console 14 is carried out by means of an interface 15, while actuation and control of the probe 12 by the surgeon is accomplished by one or more switches 23, typically located on the probe 12. One or more remote controllers, such as, for example, a footswitch 24 having additional switches 26 and 28, respectively, may also be utilized to provide the surgeon with greater control over the system 10. In response to the surgeon's manipulation of the various switches on the probe 12 and/or remote footswitch 24, the control console 14 generates and applies either a low power signal or high power signal to probe 12. As will be discussed in greater detail below, application of a low power signal to probe 12 results in coagulation of the tissue adjacent the tip 20 of the probe 12. In contrast, application of a high energy signal to probe 12 results in tissue ablation.

While operating in coagulation mode, the control console 14 of the prior art system shown in FIG. 1 is configured to drive the attached probe at a low, but constant, power level. Due to inherent varying conditions in tissue (i.e., the presence of connective tissue verses fatty tissue, as well as the presence or absence of saline solution), the impedance or load that the system experiences may vary. According to Ohm's law, a change in impedance will result in a change in current levels and/or a change in voltage levels, which in turn, will result in changing power levels. If the operating power level of the system changes by more than a predefined amount, the control console will attempt to compensate and return the power back to its originally designated level by regulating either the voltage and/or current of the power signal being generated by the console and used to drive the attached probe.

While operating in tissue ablation mode, the control console of the system shown in FIG. 1 is configured to drive the attached probe at as high a power level as possible without exceeding a maximum average power level, which in some instances may equal 400 watts.

The electrosurgical system shown in FIG. 1 modulates the entire power supply signal as a whole, turning the signal on and off in a manner similar to a pulse width modulated (PWM) signal. Furthermore, the power signal is dynamically modulated on and off so as to behave like a PWM signal having a variable duty cycle. As a result, the percentage of time that the power signal is "on", compared to the percentage of time that the signal is "off", will vary depending on the percentage of time that the power levels of the signal exceed the maximum limit over a predetermined interval of time.

Consequently, the duty cycle of the power signal is dynamically modulated so that even though the power levels of the signal may briefly exceed the maximum power limit for a portion of time during a specified interval, the average power level over that interval of time remains acceptable.

To further illustrate the above point, FIG. 2 depicts several examples of high frequency power signals generated by the control console 14 over a 20 millisecond period of time and used to drive the attached probe 12. Signal A is a power signal in the form of a 200 KHz sine wave. No modulation of signal A is present with respect to a signal duty cycle, resulting in a power signal that is continuously on (i.e., 100% duty cycle) for the entire 20 millisecond duration.

In FIG. 2, signal B is similar to signal A, but has been briefly modulated roughly half-way through the 20 millisecond period. In this instance, for example, changing environmental variables may have resulted in the power level of the signal briefly exceeding an established maximum limit during the previous 20 millisecond period (not shown). To compensate for this prior spike in power level and assure that the average power of the signal does not exceed a maximum limit, the system briefly modulates signal B during the next 20 millisecond period (shown), effectively turning the signal off for a moment. Thus, for example, signal B is modulated or turned off for approximately 5 milliseconds during the 20 millisecond period depicted, resulting in the signal effectively having a 75% duty cycle for the period shown.

To compensate for power level spikes that are larger in magnitude or longer in duration, the system dynamically modulates the duty cycle of the power signal during the next monitoring interval to effectively turn off the signal for a longer period of time. For example, signal C of FIG. 2 is similar to signal B, but is modulated to have a lower duty cycle, resulting in signal C being turned off for a longer period of time during the 20 millisecond interval shown.

By dynamically adjusting a duty cycle of the power signal, the average power of the signal can be maintained below an established maximum power limit. Furthermore, it has been observed that the ionized high energy field maintained at the tip of the probe 12 does not collapse, but remains stable, if the effective duty cycle of the power signal is modulated quickly enough (i.e., turning the signal on or off in increments of 50 milliseconds over a 1 second period).

In the electrosurgical system 10 illustrated in FIG. 1 above, the duty cycle is varied for the waveform only in instances where the voltage or current causes the power value of the RF probe to exceed the acceptable power value. Thus, in the prior art, the duty cycle is varied by differing amounts, as necessary, to account for unintended increases in power value beyond the average power value of the system.

A non-volatile memory device (not shown) and reader/writer (not shown) can be incorporated into the body 18 of the probe 12, or alternatively, incorporated into or on the cable 22 that is part of the attachable probe and which is used to connect the probe 12 to the control console 14 of the system. Alternatively, the memory device may be configured so as to be incorporated into or on the communication port that is located at the free end of the cable 22 and which is used to interface the cable with a corresponding port on the controller 14.

During manufacturing of the attachable probe shown in FIG. 1, data representing probe-specific operating parameters is loaded into the memory device. Upon connection of the attachable probe 12 to the control console 14 of the system 10, the data stored in the probe's non-volatile memory can be accessed by the reader and forwarded on to the controller 14. As such, once a probe 12 is connected, the controller 14 accesses the configuration data of the specific probe 12 and automatically configures itself based on the operating parameters of the probe 12.

Beyond probe-specific operating parameters, the prior art memory device within each attachable probe 12 can store additional data concerning usage of the probe 12. This usage data can comprise a variety of information. For example, usage data may represent the number of times a probe 12 has been used, or the duration of the time that the probe has been activated overall or at different power levels. Additional usage data may restrict the amount of time that a specific attachable probe can be used. Alternatively, a probe 12 may be programmed so it can only be used for a limited duration of time starting from the moment the probe was first attached to a control console and powered up. For example, a probe may be programmed to that it only functions for a 24-hour period starting from when the probe is first activated. Based on a clock maintained within the control console, a time stamp is written to the memory device of the probe when the probe is attached to the console for the first time and powered up. Any later attempted use of that probe will trigger a comparison of the stored time stamp to the current time reported by the control console, and if the allotted amount of time has already passed, the system will not allow the probe to be used.

Alternatively, a specific prior art probe is dynamically restricted, so that the overall amount of time allocated for use of the probe will vary depending not only on the amount of time the probe has been used, but also the power levels that the probe was driven at during its use. As such, a specific attachable probe may be limited to 1 hour of use if always driven at a maximum power, but may be usable for 3 hours if all prior uses occurred at substantially lower power levels.

In addition to usage data, the prior art memory device can store information concerning any errors that were encountered during use of the probe 12. For example, the failure of a probe to activate would lead the control console 14 to issue and store one or more error codes into the probe memory. Technicians can later retrieve these error codes to aid in their examination of the failure.

In addition to probe-specific operating parameters and usage data, the memory device incorporated into each probe may also be programmed by the manufacturer to include software scripts or updates for the control console of the system.

In the electrosurgical system illustrated in FIG. 1, the power output from control console 14 has a constant source impedance regardless of the probe utilized or the mode of operation.

As discussed above, the electrosurgical system 10 shown in FIG. 1 provides a modulated duty cycle power output only to decrease power output in instances where the power exceeds the desired power due to incidental variations in the impedance of the load or other power control issues. Further, the duty cycle value varies depending on the amount that the power exceeds the desired average power level. Thus, during normal operation, the output power value may, in some instances, not exceed the desired intended constant average power value resulting in no duty cycle variations in the power output by an energy generator.

The present invention is directed to improving cutting or coagulation of tissue by an RF probe, such as by optimizing power delivery to tissue by adjusting the source impedance value of an RF generator.

In one embodiment of the invention, information regarding source impedance values for an RF generator is stored on an RF probe and read by a processing device. The processing device controls the source impedance value of the RF generator based on the stored values to optimize power transfer from the RF generator to tissue via the RF probe.

In another embodiment of the invention, improved operation of an electrosurgical system is obtained by duty cycling of voltage output from a RF generator to increase the instantaneous voltage value applied to an RF probe. The duty cycling information is read from a memory device on the RF probe. Modulating the RF voltage value at a secondary frequency with a duty cycle of less than 100% reinitiates a voltage arc dynamically on different tissues at the beginning of each time period that includes the duty cycle value. Periodically reinitiating arcing by duty cycling the RF output voltage value helps to maintain consistent burn characteristics on various tissues. Also, constant duty cycling tends to physically push tissue away from the probe tip during ablation to maintain good spacing between the probe tip and tissue, which creates optimal arcing, and thus helps to prevent clogging. Further, the duty cycling of output voltage helps to control depth of necrosis because the heated tissue is allowed to thermally relax between each duty cycle application of RF voltage.

Another advantage of the invention is that the duty cycle applied to the RF voltage output decreases the amount of total time the probe is exposed to high RF voltage, which reduces probe degradation as compared to a continuous application of RF power. In this embodiment, cyclically applying voltage to the RF probe at less than the maximum allowable voltage value, or even at the same voltage value as a non-duty cycled RF generator output, reduces heating of the surgical site, such as a joint, without significantly affecting cutting performance.

DETAILED DESCRIPTION

Figure 3:
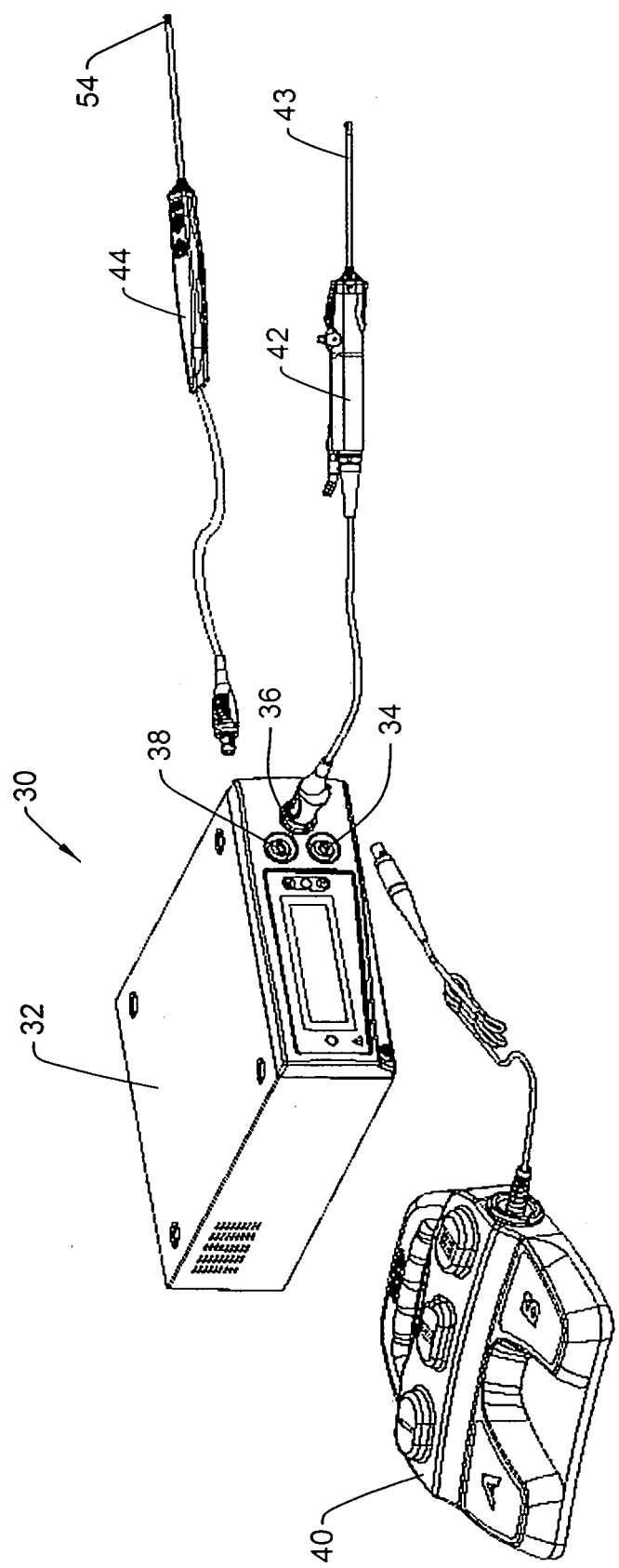
FIG. 3 depicts an electrosurgical system of the invention that includes a footswitch, an electrosurgical probe and a powered surgical handpiece for attachment to a control console.

FIG. 3 shows a surgical system 30 including a console 32 having a footswitch receiving port 34, a handpiece receiving port 36 and a RF probe receiving port 38. The footswitch receiving port 34 provides a connection to the control console 32 for a footswitch 40. Handpiece receiving port 36 receives the connection jack of a powered surgical handpiece 42 with a cutting element or burr 43 attached thereto. One conventional handpiece is disclosed in U.S. Patent Publication No. 2003/0093103, the disclosure of which is hereby incorporated by reference herein. RF probe receiving port 38 receives a connecting jack of an RF probe 44.

Figure 4:
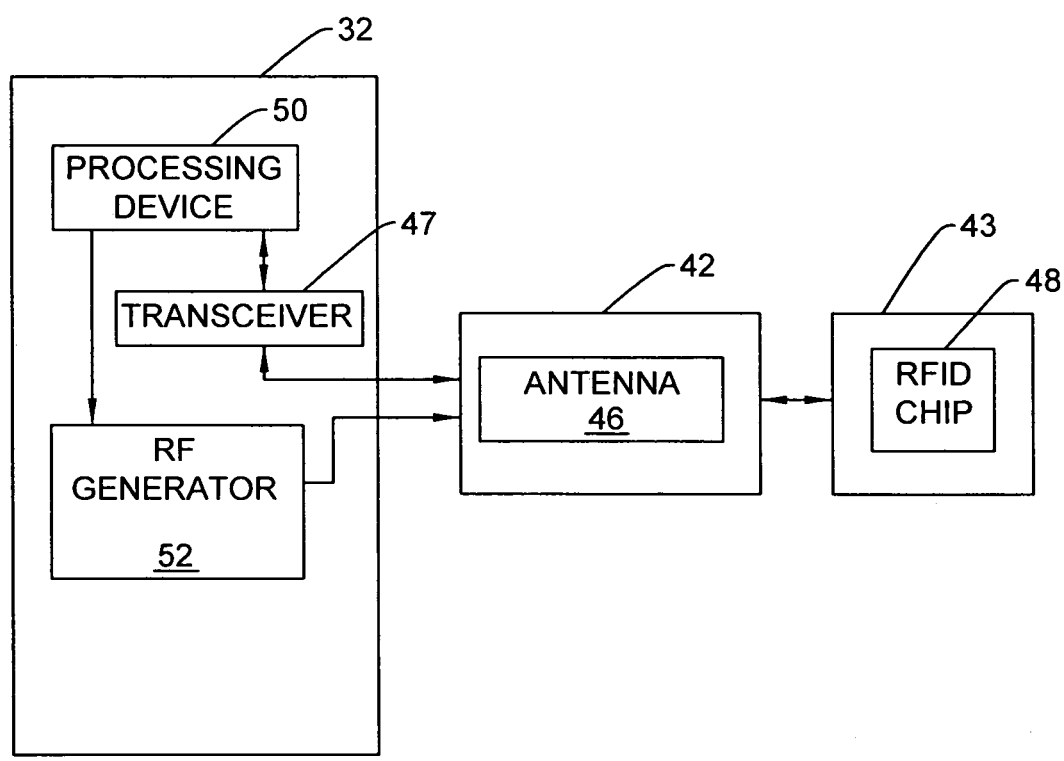
FIG. 4 is a block diagram illustrating components of the control console and the powered handpiece of FIG. 3.

As shown in FIG. 4, the powered handpiece 42 of the surgical system 30 includes an antenna 46. In one embodiment, a non-volatile memory device, such as an RFID chip 48, is provided in the cutting element 43. A transceiver 47 located in the control console 32 is connected to the antenna 46 for reading probe-specific data. Antenna 46 carries power from the transceiver 47 to the RFID chip 48 in the cutter element 43 and returns data from the chip to the transceiver. In some embodiments, the transceiver 47 also writes data to the RFID chip 48.

Figure 1:
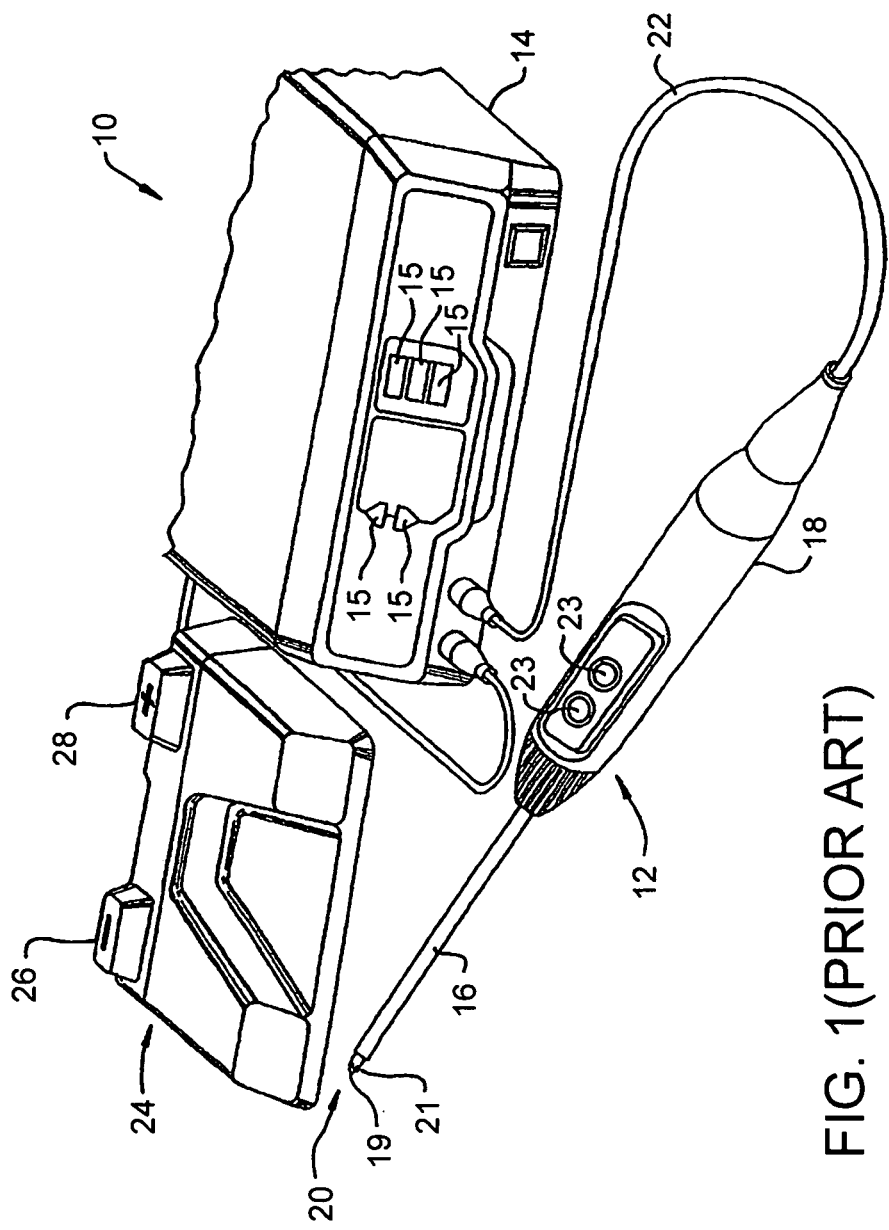
FIG. 1 depicts an electrosurgical system that includes an electrosurgical probe connected to a control console, along with a footswitch.
Figure 2:
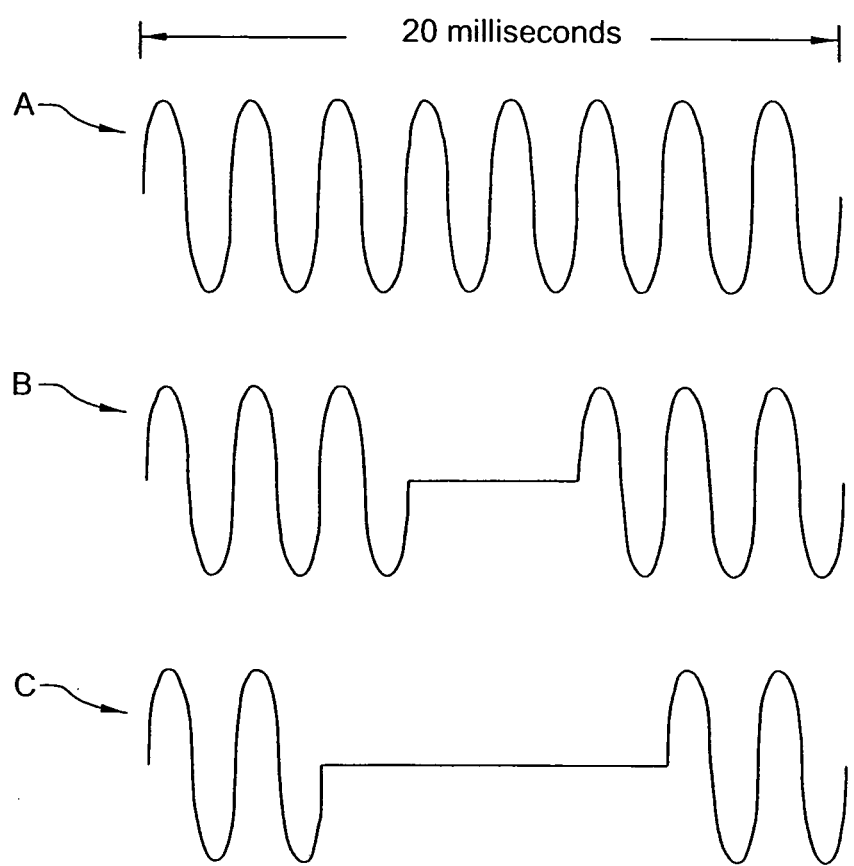
FIG. 2 depicts examples of high frequency RF signals generated by the control console shown in FIG. 1 for driving the attached probe.

One embodiment of the RF probe 44 generally corresponds to the probe structure illustrated in FIG. 1, except additional probe-specific data, described later herein, is provided on a one-wire memory device and provided to the control console 32. The console 32 includes a processing device 50 for processing the data received from the one-wire memory device. The processing device 50 controls an RF generator 52 that provides RF energy to the RF probe 44 to power an electrode 54 at the distal end thereof. In one embodiment, the RF probe 44 and the electrode 54 form a disposable unit.

The embodiments of FIGS. 3 and 4 include the powered handpiece receiving port 36 that enables the control console 32 to provide power to surgical handpiece 42. The surgical handpiece 42 enables mechanical cutting and debridement of bone and soft tissue.

RF Generator Source Impedance

Figure 5:
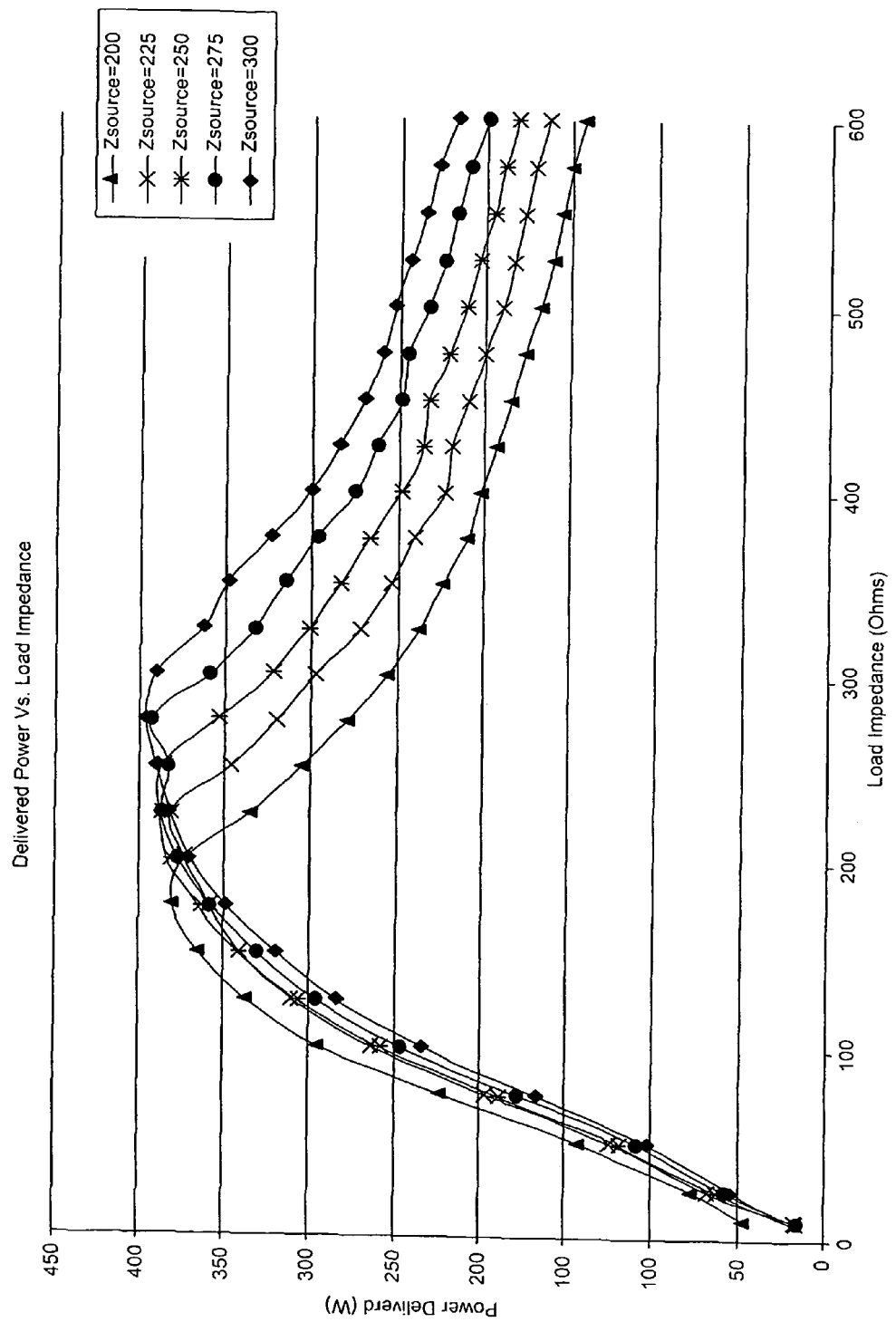
FIG. 5 illustrates a graph showing delivered power versus load impedance for a number of different source impedances of an RF generator.

FIG. 5 shows a graph plotting power delivered (watts) versus load impedance $Z_L$ (ohms) for a single electrosurgical probe. The graph shows power delivered values versus load impedance values for five different RF generator source impedances $Z_{source}$ as represented by respective plotted lines on the graph. The source impedance values $Z_{source}$ are 200Ω, 225Ω, 250Ω, 275Ω and 300Ω.

In general, when the load impedance is low, the power delivered is low to prevent a large current from passing through the electrode 54. Such a large current may cause electric shock or other dangerous conditions and thus is prevented by current limiting circuitry in the RF generator 52.

Different RF probes 44, due to their shape, size or other factors, result in different load impedances $Z_L$ provided to the console for the same tissue type or tissue characteristics. Thus the RF generator 52 may provide optimal delivered power for the RF probes, as shown in FIG. 5, by adjusting the source impedance.

The load impedance value $Z_L$ is also affected greatly by whether the tissue is being cut or the tissue is being coagulated. Further, the temperature of the joint being operated on and the amount of fluid in the joint also can affect the load impedance value $Z_L$.

Since various RF probes 44 are intended for use in various surgical operations, the load impedance range of use for cutting is predictable. Thus, the source impedance value $Z_{source}$ that provides the highest delivered power in the expected load impedance range is stored in the RFID memory chip 48 and is provided to the processing device 50. Therefore, different source impedance values $Z_{source}$ are provided for various different RF probes 44 depending on the probe structure and the intended use of the probe.

In some embodiments, the RFID chip 48 includes one or more values for the source impedance of the RF generator 52 for use with the particular probe. For instance, one source impedance value, such as 200Ω, may be provided for a coagulation operation and another source impedance value, such as 250Ω, may be provided for the RF generator 52 when the RF probe 44 is utilized for cutting tissue or ablation.

Figure 6:
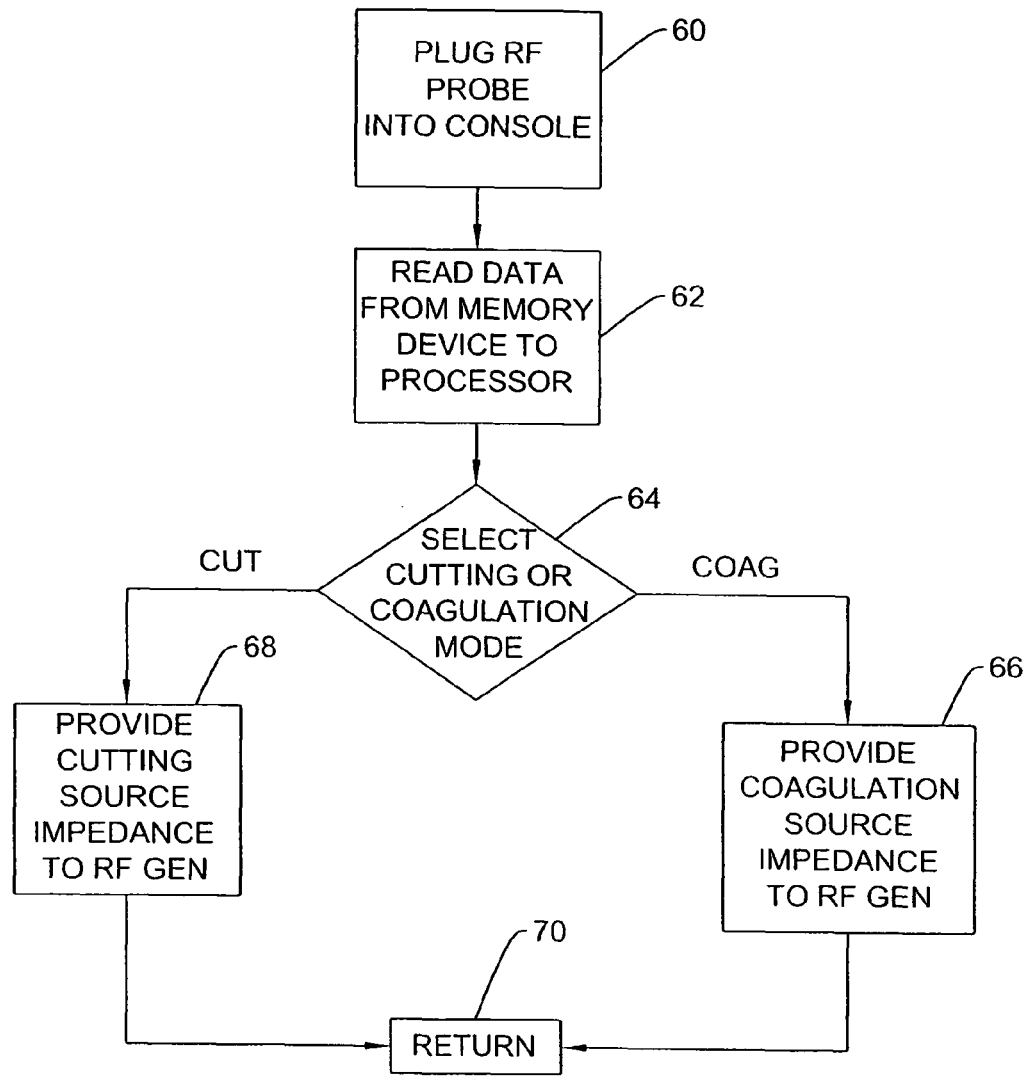
FIG. 6 is a flowchart showing steps for configuring of an RF generator with a predetermined source impedance value depending on selected operating modes.

Operation of one embodiment of a surgical system 30 having dynamic source impedance values $Z_{source}$ is illustrated in FIG. 6. At step 60, the jack or connector of the RF probe 44 is inserted into the corresponding probe receiving port 38 on the control console 32. Then, at step 62, the processing device 50 of the console 32 automatically receives the probe data stored in the RFID chip 48. The probe data includes RF generator source impedance values $Z_{source}$ for different operating conditions of the specific RF probe 44. At step 64, the user then selects either a cutting mode or a coagulation mode. If a coagulation mode is selected, the processing device 50 advances to step 66. At step 66, the processing device 50 operates on circuitry within the control console 32 to provide a stored coagulation source impedance value $Z_{source}$ to the RF generator 52 for the coagulation mode. Then, at step 70, the processing device 50 returns to a control mode wherein the RF generator 52 is selectively controlled by a user to apply RF energy and coagulate tissue or veins.

If the cutting mode is selected at decision step 64, the processing device 50 advances to step 68. At step 68, the processing device 50 controls circuitry so that the RF generator 52 is provided with a cutting source impedance value $Z_{source}$ that was previously read by the processing device 50 from the RFID chip 48. Therefore, as illustrated in FIG. 6, in operation, the RF generator 52 is provided with a source impedance value $Z_{source}$ that maximizes the power delivered during operation of the RF probe 44 in either operating mode.

Increasing Instantaneous Power

As discussed above, in many surgical devices the maximum amount of power mandated for use with a probe is 400 watts per second. Some embodiments of the invention provide a greater instantaneous power to tissue while maintaining the overall specified average power of, for example, 400 watts/second. Some embodiments provide RF power to the probe 44 at a specified predetermined constant duty cycle of a time period T defined by a secondary frequency value f that is less than the RF frequency. Specifically, time period T is the inverse of the frequency f and thus equals 1/f. Therefore, instantaneous power delivered can be increased without exceeding a maximum total power requirement for a given time period.

This approach for increasing the instantaneous power is described by the equation set forth below.

$$P_{inst} = P_{ave} \div \text{duty cycle \%}$$

In the above equation, $P_{ave}$ is P an average constant continuous power value that provides maximum allowable power to an electrosurgical probe, such as 400 watts per second. $P_{inst}$ is a maximum instantaneous power value greater than the constant continuous average power $P_{ave}$. $P_{inst}$ is determined by $P_{ave}$ and a duty cycle percent value. The smaller the duty cycle value, the greater the value for $P_{inst}$.

Figure 7:
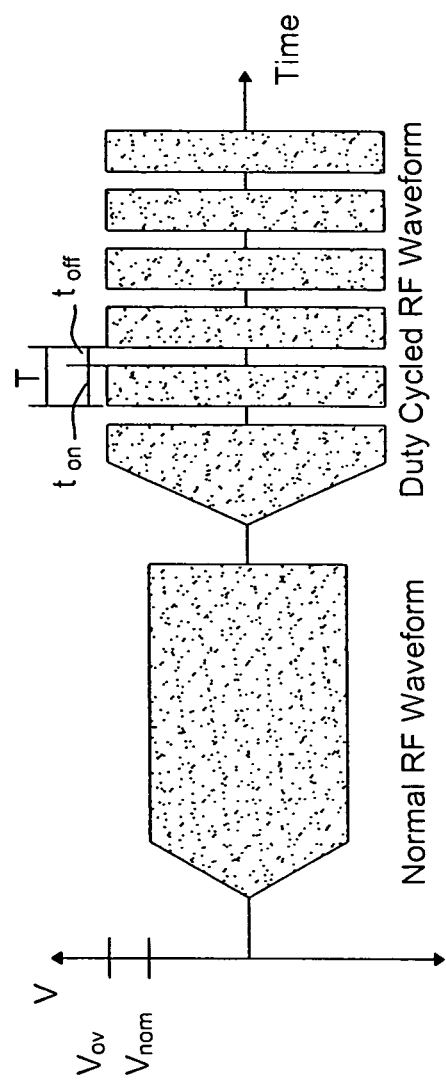
FIG. 7 is a graph illustrating a normal RF waveform and a duty cycled RF waveform.

In FIG. 7, a normal RF waveform has a constant voltage value Vnom, which at a constant load impedance value $Z_L$ provides a constant average power value $P_{ave}$. Thus, after the beginning start-up of voltage applied to the RF probe 44, nominal voltage $V_{nom}$ is applied continuously, to obtain the constant average power value $P_{ave}$ for the entirety of the illustrated normal RF waveform.

An improvement in power applied to an RF probe 44, at least under certain conditions, is illustrated by the duty cycled RF waveform also shown in FIG. 7. As discussed above, the duty cycled waveform has a time period T that is defined by the inverse of the secondary frequency value f. As discussed above, the secondary frequency value f must be much less than the RF frequency value applied to the RF probe 44. The secondary frequency value, in some embodiments, has a value of 20 Hz.

The over voltage value $V_{ov}$ shown in FIG. 7 at a constant load impedance value $Z_L$ provides the instantaneous maximum power value $P_{inst}$ described above. The over voltage value $V_{ov}$ is greater than the voltage value $V_{nom}$ as a result of the off portion $t_{off}$ of each time period T. Thus, voltage value $V_{ov}$ shown in FIG. 7 and applied to RF probe 44 by the RF generator 52 results in an instantaneous power value $P_{inst}$ that is greater than a corresponding average power value $P_{ave}$ even though total power over time periods T is about the same.

In FIG. 7, the duty cycle $t_{on}$ is approximately 75% of the period T and the off portion $t_{off}$ is approximately 25% of the time period T. If the constant duty cycle were decreased from 75% to 50% in another embodiment, the over voltage value $V_{ov}$ applied for each duty cycle would then increase resulting in an increase in the instantaneous power value $P_{inst}$ as set forth in the above power equation. Again, the embodiment illustrated in FIG. 7 is plotted with the load impedance value $Z_L$ having a constant value for the entirety of the time illustrated along the length of the x-axis.

If there are changes in load impedance $Z_L$ along the time axis shown in FIG. 7 for the duty cycled RF waveform, the overvoltage value $V_{ov}$ generally is maintained and thus the instantaneous power value $P_{inst}$ for the duty cycle $t_{on}$ of each time period T may vary slightly. Thus the $Z_{source}$ value must be as close as possible to $Z_{Load}$ to maximize power output from the RF probe 44.

As in the source impedance embodiment discussed above, maximum power and duty cycle control information can be stored in the memory device, along with other RF probe data, as well as source impedance values $Z_{source}$.

Figure 8:
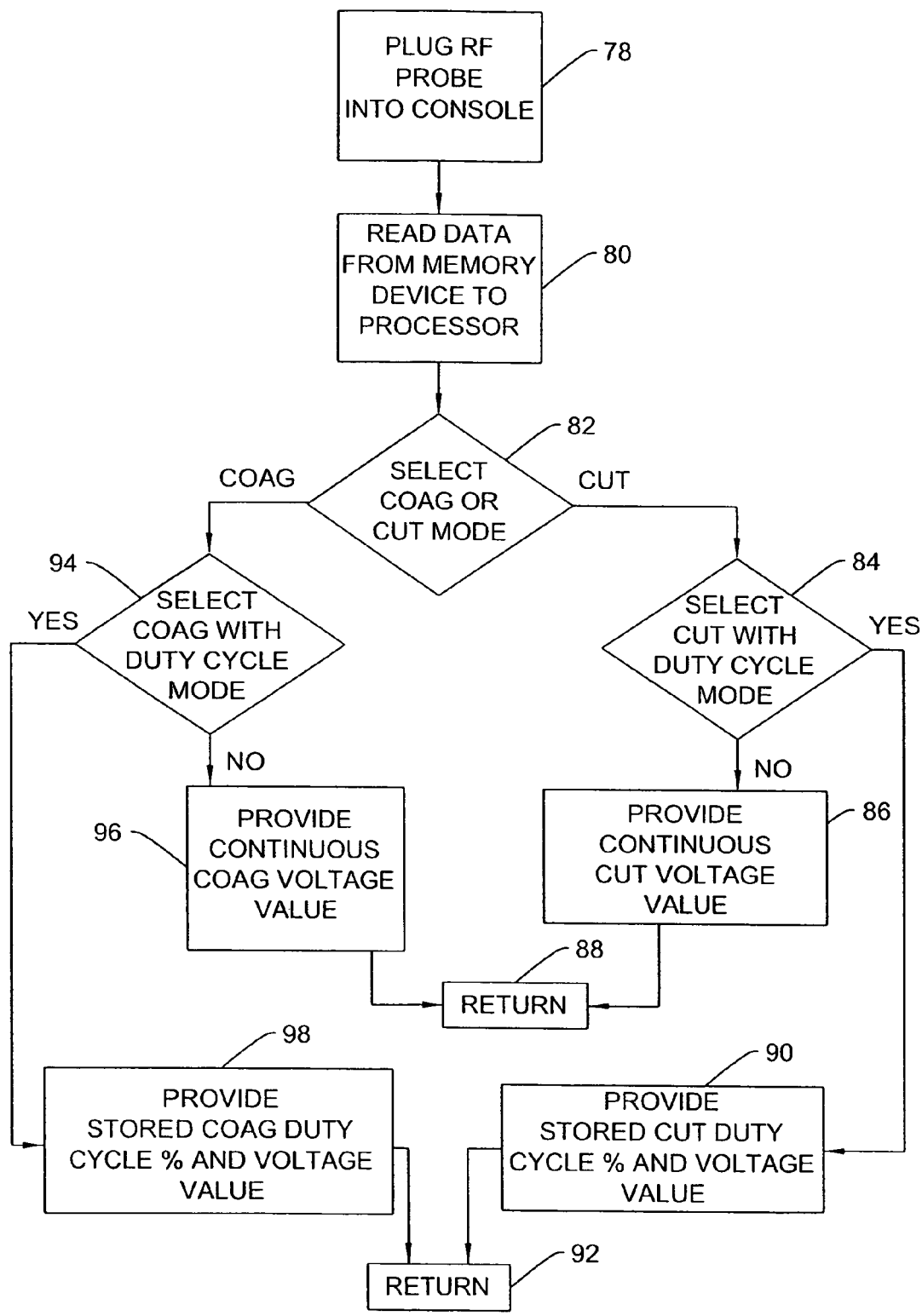
FIG. 8 is a flowchart showing selection of a continuous operation or duty cycled operation of an RF generator after selection of a coagulation or cutting mode.

Operation of the RF probe 44 in the instantaneous increased power arrangement having a duty cycled RF waveform is explained in the flow chart of FIG. 8. In step 78 of FIG. 8, the RF probe 44 is plugged into the RF probe receiving port 38. At step 80, probe-specific data is read from the memory device by the processing device 50. In some embodiments, probe data read by the processing device 50 disposed in the console 32 includes probe-specific duty cycle values for both coagulation modes and cut modes. In some embodiments, a secondary frequency value is also provided. In some embodiments, a probe-specific constant voltage value for a continuous coagulation mode can be provided.

At decision step 82, the user selects either the coagulation mode or the cutting mode. If the cutting mode is selected, the processing device 50 advances to decision step 84. At decision step 84, a user selects between cutting with a duty cycle or operating at a continuous voltage cut value. If the user selects operation at a continuous voltage cut value, the processor 50 advances to step 86 and in view of the probe data controls the RF generator 52 to output the non-duty cycle maximum average voltage $V_{nom}$. Then, at step 88, the processing device 50 returns to enable powering of the RF generator 52 by a user at the continuous voltage cut value, corresponding to the maximum average power value $P_{ave}$.

If the operator decides to cut tissue with a duty cycle arrangement at step 84, the processing device 50 advances to step 90. At step 90, the processor device 50 calculates instantaneous power value $P_{inst}$ from the stored duty cycle percentage value read from the memory device and the average power value $P_{ave}$. The processor device 50 then calculates an expected over voltage value $V_{ov}$ that is intended to result in the instantaneous power value $P_{inst}$ during the duty cycle. The processing device 50 then advances to step 92 and returns to enable operation in the duty cycled cutting mode.

Returning to step 82, if the operator selects the coagulation mode, the processing device 50 advances to decision step 94. At decision step 94, if the user selects operating the RF probe 44 at a continuous coagulation power value, the processor device 50 advances to step 96 and configures or controls the RF generator 52 for operation at an essentially constant continuous voltage value that coagulates tissue and then returns at step 88 to permit operation of the RF probe 44.

At decision step 94, if the user decides to perform coagulation with a duty cycled value, the processing device 50 advances to step 98. At step 98, a coagulation duty cycle power value is obtained by dividing the average desired coagulation power value by a duty cycle value received by the processing device 50 from the memory device. The instantaneous power value is then converted to a coagulation operating voltage and output by the RF generator 52 for the duty cycle $t_{on}$ of the time period T.

As with the above embodiments directed to RF generator source impedance values $Z_{source}$ discussed above, in these additional embodiments the secondary frequency value f, and especially the stored duty cycle values may vary for different types of probes and may also vary for the coagulation mode and the cutting mode for any given RF probe. In other embodiments, the secondary frequency value f is a constant value for all RF probes and is stored in the processing device 50.

While FIG. 8 shows manual selection of a continuous essentially constant voltage value or of a duty cycled voltage value provided to an RF probe 44, in another embodiment a duty cycled power value is output from the RF probe automatically in the coagulation mode. In other embodiments, a continuous constant voltage is output by the RF generator in every instance that the coagulation mode is selected.

While FIG. 8 does not show the selection of a source impedance value, the value $Z_{source}$ can be provided to control the RF generator 52 along with the stored duty cycle value at step 90 or at step 98.

While the disposable RF probe 44 is disclosed as having a one-wire memory device or an RFID chip, other non-volatile memory devices are also contemplated.

In another embodiment of the invention, the normal nominal voltage value $V_{nom}$ illustrated in FIG. 7 for a continuous mode, operates as an RF generator 52 output voltage value $V_{nom}$ during on periods $t_{on}$ of a duty cycle. This embodiment has an improved cooling effect on the tissue and arc reinitiation provides a desired cutting effect despite a lesser amount of voltage being applied to the tissue over time period T.

In another embodiment of the invention, a voltage value between $V_{nom}$ and $V_{ov}$ having a duty cycle is applied to the RF probe 44. This voltage value, determined by the processor device 50, maximizes performance by providing cooling during time $t_{off}$ while providing a voltage value greater than or equal to $V_{nom}$ during $t_{on}$.

In another embodiment of the invention, a blend mode providing simultaneous cutting and coagulation of tissue may be provided by the RF generator 52. In this arrangement, a specific source impedance value that is different from the source impedance value for other modes is contemplated.

In some embodiments, the RF probe 44 has a bipolar electrode and in other embodiments the RF probe has a monopolar electrode.

In some embodiments, the handpiece structure of the RF probe 44 is not disposable. In these embodiments the electrode 54 projecting from the distal end of the probe body is detachably coupled to the probe body.

Although particular preferred embodiments of the invention are disclosed in detail for illustrative purposes, it will be recognized that variations or modifications of the disclosed apparatus, including the rearrangements of parts, lie within the scope of the present invention.

What is claimed is:

1. Method of controlling source impedance of an RF generator in a control console for an electrosurgical system including an electrosurgical RF probe, the control console being in communication with a memory device associated with the RF probe, the method comprising the steps of:
  connecting the electrosurgical RF probe to the control console having the RF generator, the memory device associated with the RF probe providing probe-specific data stored in the memory device to a processing device in the control console, the probe data comprising at least a first source impedance value corresponding to a coagulation operating mode for the RF probe and a second source impedance value corresponding to a cutting operating mode for the RF probe;
  selecting the coagulation operating mode or the cutting operating mode, the processing device operating so that the source impedance of the RF generator has a source impedance value corresponding to the first source impedance value when the coagulation operating mode is selected by an operator and so that the source impedance of the RF generator has the second source impedance value when the cutting operating mode is selected by an operator; and
  operating the RF probe to coagulate or cut tissue at a surgical site.

2. The method of claim 1, wherein the RF probe comprises a first RF probe, and wherein at least one of the first and second source impedance values stored in the memory device associated with the first RF probe is different from at least one of corresponding first and second source impedance values stored in a memory device associated with a second RF probe.

3. The method of claim 1, wherein the probe-specific data provided to the processing device comprises a maximum voltage average value and a constant duty cycle value for the RF probe.

4. The method of claim 1, wherein the first source impedance value is different than the second source impedance value and the first source impedance value is different than a load impedance value at the surgical site.

5. The method of claim 1, wherein the probe specific data comprises a third source impedance value for the RF generator corresponding to a blend mode for providing simultaneous cutting and coagulation of tissue.

6. The method of claim 5, wherein the third source impedance value is different from the first source impedance value and the second source impedance value.

7. The method of claim 1, wherein the RF probe comprises a bipolar electrode.

8. The method of claim 1, wherein the RF probe comprises a monopolar electrode.

9. The method of claim 1, wherein current output from the RF probe operating at the first or the second source impedance value passes through the tissue at the surgical site having a load impedance value.

10. The method according to claim 1, wherein the first source impedance value is different than the second source impedance value, and wherein a load impedance value at the surgical site is affected by whether the tissue is being cut or coagulated by the RF probe at the surgical site, by temperature at the surgical site, and by amount of fluid at the surgical site, the first and second source impedance values being provided to maximize power output by the RF probe for the load impedance value.

11. The method according to claim 10, wherein the first source impedance value comprises about 200 ohms and the second source impedance value comprises about 250 ohms.

12. Method of controlling source impedance of an RF generator in a control console for an electrosurgical system including an electrosurgical RF probe during cutting or coagulating of tissue, the control console being in communication with a memory device associated with the RF probe, the method comprising the steps of:
   connecting the electrosurgical RF probe to the control console having the RF generator, the memory device associated with the RF probe providing probe-specific data stored in the memory device to a processing device in the control console, the probe data comprising a first source impedance value corresponding to a coagulation operating mode for the RF probe, a second source impedance value corresponding to a cutting operating mode for the RF probe, a maximum continuous average voltage value and a constant duty cycle value of less than 100% and corresponding proportionally to a time period defined by a secondary frequency value, the processing device having a maximum instantaneous voltage value based on the probe data;
   selecting the coagulation operating mode or the cutting operating mode, the processing device operating so that the source impedance of the RF generator has a source impedance value corresponding to the first source impedance value when the coagulation operating mode is selected by an operator and so that the source impedance of the RF generator has the second source impedance value when the cutting operating mode is selected by an operator; and
   operating the RF probe at the second source impedance value to output an instantaneous voltage value in a range that is greater than the maximum continuous average voltage value and that is not greater than approximately the maximum instantaneous voltage value to the RF probe to cut tissue during the constant duty cycle value which comprises a first portion of the time period, and wherein no voltage value is output by the RF generator or applied to the RF probe during a second remaining portion of each said time period.

13. The method of claim 12, wherein the RF probe comprises a first RF probe with a first constant duty cycle, and wherein a second electrosurgical RF probe different from the first RF probe is provided having a constant duty cycle value that is different from the first duty cycle value of the first probe.

14. The method of claim 12, wherein the first source impedance value is different than the second source impedance value.

15. Method of controlling source impedance of an RF generator in a control console for an electrosurgical system including an electrosurgical RF probe, the control console being in communication with a memory device associated with the RF probe, the method comprising the steps of:
   connecting the electrosurgical RF probe to the control console having the RF generator, the memory device associated with the RF probe providing probe-specific data stored in the memory device to a processing device in the control console, the probe-specific data comprising at least a first source impedance value for the RF generator and a second source impedance value different than the first source impedance value for the RF generator;
   selecting an operating mode, wherein the processing device is configured so that the source impedance of the RF generator has the first source impedance value when a first operating mode is selected by an operator and the RF generator has the second source impedance value when a second operating mode is selected by an operator; and
   operating the RF probe to treat tissue at a surgical site, wherein a load impedance value at the surgical site is dependent on at least power output by the RF generator, RF probe characteristics, tissue characteristics at the surgical site, temperature at the surgical site and the amount of fluid at the surgical site.

16. The method of claim 15, wherein the first operating mode comprises a coagulation operating mode and the first source impedance value maximizes power output by the RF generator for the RF probe during coagulation.

17. The method of claim 16, wherein the second operating mode comprises a cutting operating mode and the second source impedance value maximizes power output by the RF generator for the RF probe during cutting of tissue.

18. The method of claim 15, wherein the RF probe comprises a first RF probe, and wherein at least one of the first and second source impedance values stored in the memory device associated with the first RF probe is different than corresponding first and second source impedance values stored in a memory device associated with a second RF probe.

19. The method of claim 15, wherein the first source impedance value comprises about 200 ohms.

20. The method of claim 15, wherein the probe specific data stored in the memory device comprises a third source impedance value for the RF generator corresponding to a blend mode for providing simultaneous cutting and coagulation of tissue, and wherein the third source impedance value is different than the first source impedance value and the second source impedance value.

* * * * *